United States Patent [19]
McCarthy et al.

[11] Patent Number: 4,496,725
[45] Date of Patent: Jan. 29, 1985

[54] SUBSTITUTED 1,2,3-TRIAZINO[4′,5′:4,5]-THIENO[2,3-B]QUINOLIN-4(3H)-ONES

[75] Inventors: James R. McCarthy, Zionsville, Ind.; Paul J. Widner, Landenberg, Pa.

[73] Assignee: The Dow Chemical Company, Midland, Mich.

[21] Appl. No.: 496,800

[22] Filed: May 23, 1983

[51] Int. Cl.³ .......................................... C07D 495/12
[52] U.S. Cl. .................................................. 544/184
[58] Field of Search ........................ 544/184; 544/184

[56] References Cited

U.S. PATENT DOCUMENTS 4,239,887 12/1980 Youssefyeh ........................ 544/184

OTHER PUBLICATIONS

Schneller et al., Heterocycles, vol. 3, pp. 135–138, (1975).
Beck et al., J. Org. Chem., vol. 41, pp. 1733–1734, (1976).

Primary Examiner—John M. Ford
Attorney, Agent, or Firm—John J. Kolano; Gary D. Street; Richard G. Waterman

[57] ABSTRACT

Substituted 1,2,3-triazino[4′,5′:4,5]thieno[2,3-b]quinolin-4(3H)-ones useful as antiallergic agents are described herein. The compounds are prepared by the reaction of an appropriate substituted 3-aminothieno[2,3-b]quinoline-2-carboxamide with sodium nitrite in an acid such as acetic acid.

2 Claims, No Drawings

SUBSTITUTED 1,2,3-TRIAZINO[4',5':4,5]-THIENO[2,3-b]QHINOLIN-4(3H)-ONES

The present invention is directed to a group of substituted 1,2,3-triazino[4', 5':4,5]thieno[2,3-b]-quinolin-4(3H)-ones. More particularly, it is directed to compounds of the following general formula

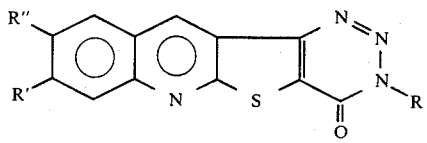

wherein R is hydrogen or lower alkyl of 1-4 carbon atoms; R' and R'' are hydrogen or methoxy with the proviso that at least one must be methoxy, or R' and R'' are combined as methylenedioxy. Examples of the alkyl groups referred to above are methyl, ethyl, propyl or butyl.

Equivalent for the purposes of this invention are the pharmaceutically acceptable salts. The term "pharmaceutically acceptable salt" as used herein is intended to include non-toxic cationic and anionic salts. The anionic salts include both of those formed by the addition of inorganic acids such as hydrochloric or hydrobromic acid or by the addition of organic acids such as acetic acid and propionic acid. Cationic salts are formed only with those compounds wherein R is hydrogen. They are intended to include non-toxic cationic salts such as the alkali metal salts, e.g., sodium and potassium; alkaline earth metal salts, such as calcium, magnesium or barium; salts with ammonia; and salts with organic bases, e.g., amines such as triethylamine, n-propylamine and tri-n-butylamine.

The compounds of the present invention are prepared from an appropriate tricyclic aminocarboxamide having the following structural formula

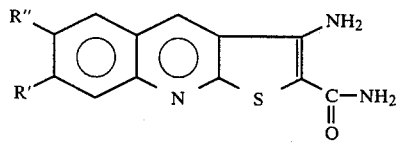

wherein R' and R'' are defined as above. This compound is reacted with sodium nitrite in acetic acid. Under these conditions, diazotization of the amine nitrogen and cyclization takes place to give those compounds of the present invention wherein R is hydrogen. To obtain the compounds wherein R is $C_{1-4}$ lower alkyl, those compounds wherein R is hydrogen are reacted with a strong base, usually an alkali metal base, to give the corresponding salts, followed by reaction with a $C_{1-4}$ lower alkyl halide, preferably the bromide or iodide, to give the desired alkyl-substituted compounds.

The starting material referred to above is obtained from an appropriately substituted 2-chloro-3-quinolinecarboxaldehyde. The carboxaldehyde is reacted with hydroxylamine (hydrochloride) to give the corresponding oxime which is then dehydrated with an appropriate reagent such as acetic anhydride to give the corresponding substituted 2-chloro-3-quinolinecarbonitrile. The carbonitrile is then reacted with 2-mercaptoacetamide under alkaline conditions to give the desired aminocarboxamide.

The substituted 2-chloro-3-quinolinecarboxaldehydes used as the original starting materials in the process as described above are themselves known compounds as described by O. Meth-Cohn et al., Tetrahedron Letters, 311 (1979) or they are obtained from an appropriate substituted acetanilide by appropriate procedures as described in the indicated article by Meth-Cohn et al.

The compounds of the present invention possess anti-allergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermatitis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maize-starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as Remington's Pharmaceutical Sciences, Mack Publishing Company, Easton, Pennsylvania.

The compounds of the present invention or pharmaceutical compositions thereof may be administered to human asthmatic patients in single oral doses of approximately 1-1000 mg of active ingredient and multiple oral doses totaling up to about 4000 mg/day of active ingredient. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The antiallergic activity of the present compounds is demonstrated by the IgE mediated rat Passive Cutaneous Anaphylaxis (PCA) test. This test is generally accepted as one of the best animal models for the qualitative determination of antiallergic activity. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.
2. Animals—Adult male Sprague-Dawley or female Wistar Kyoto rats were used as antisera recipients in the test. The animals were allowed to acclimate for 5–14 days with food and water ad lib.
3. Sensitization—Recipient rats were passively sensitized by the intradermal injection of 100 microliters of two dilutions of antiserum (one injection on each side of the back). Sensitization occurred 48–72 hours prior to antigen challenge.
4. Administration of Test Compound—Four to six animals were used for each test compound/dilution. Compounds were homogenized in an appropriate carrier solution, and administered i.p. at 60 mg/kg 5 minutes prior to challenge or p.o. at 100 mg/kg 5 to 240 minutes prior to challenge.
5. Antigen Challenge and Reaction Evaluation—Ovalbumin (0.1–1.0 mg in a 0.5% solution of Evan's Blue dye) in saline was given to each rat by i.v. administration. Thirty minutes later, the resultant PCA reactions were measured for average diameter and color intensity from the reflected surface of the skin. Test compound activity is expressed as percent inhibition based on control reactions. When tested by the above procedure, the compounds of the present invention were active both i.p. and orally.

In addition to activity in the PCA test as described above, the compounds of the present invention also inhibit the release of histamine in the rat Passive Peritoneal Anaphylaxis (PPA) test. This method can be described briefly as follows:

PPA Test Method

1. Antisera—Reaginic antibody to ovalbumin for this test was prepared in adult male $B_6D_2F_1$ mice.
2. Animals—Adult male Sprague Dawley or female Wistar Kyoto rats were used as antibody recipients. The animals were allowed to acclimate for 5–14 days with food and water ad lib.
3. Sensitization—Recipient rats were sensitized i.p. with 2 ml of an appropriate saline dilution of the mouse anti-ovalbumin antiserum determined from prior experiments. Sensitization took place 2 hours prior to antigen challenge.
4. Administration of Test Compound—Five to ten animals were used for each test compound/dilution. Compounds were homogenized in saline with an equivalent of sodium bicarbonate to effect solubilization, if appropriate, and administered i.p. at 60 µg, 30 seconds prior to antigen challenge or p.o. 5 to 60 minutes prior to antigen challenge.
5. Antigen Challenge and Assay Evaluation—Two mg of ovalbumin in 5 ml of modified Tyrode's Solution was administered by i.p. injection and the animals were sacrificed 5 minutes later. Peritoneal shock fluids were collected and classified by centrifugation. Protein was removed from the samples by perchloric acid precipitation and subsequent centrifugation. The samples were then analyzed for histamine content by an automated fluorometric assay. Histamine levels of peritoneal shock fluids from treatment animals were then compared to those of shock fluids from control animals. Drug effect was expressed as percent inhibition of histamine release.

The following examples are presented to illustrate the present invention but they should not be construed as limiting in any way.

EXAMPLE 1

To 50 g of 2-chloro-6,7-dimethoxy-3-quinolinecarboxaldehyde was added 50 g of hydroxylamine hydrochloride in 500 ml of pyridine. The mixture was stirred at room temperature for 16 hours and the solvent was then evaporated to leave a semi-solid material. This was washed with water, filtered and recrystallized from dimethylformamide to give 2-chloro-6,7-dimethoxy-3-quinolinecarboxaldehyde oxime melting at about 237°–237.5° C. with decomposition.

If 2-chloro-6-methoxy-3-quinolinecarboxaldehyde and 2-chloro-6,7-methylenedioxy-3-quinolinecarboxaldehyde are each reacted with hydroxylamine hydrochloride according to the above procedure, the corresponding oximes are obtained.

EXAMPLE 2

To 112 g of 2-chloro-6,7-dimethoxy-3-quinolinecarboxaldehyde oxime was added 1000 ml of acetic anhydride. The mixture was stirred at reflux for 3 hours and then cooled to room temperature. The precipitate which formed was separated by filtration, washed with hot ethanol, and then dried to give 2-chloro-6,7-dimethoxy-3-quinolinecarbonitrile melting at about 223.5°–224.5° C.

2-Chloro-6,7-methylenedioxy-3-quinolinecarboxaldehyde oxime and 2-chloro-6-methoxy-3-quinolinecarboxaldehyde oxime are each reacted with acetic anhydride according to the above procedure to give, respectively, 2-chloro-6,7-methylenedioxy-3-quinolinecarbonitrile and 2-chloro-6-methoxy-3-quinolinecarbonitrile.

EXAMPLE 3

To a mixture of 20 g of 2-chloro-6,7-dimethoxy-3-quinolinecarbonitrile in 500 ml of dimethylformamide was added 20 g of 2-mercaptoacetamide. To the resultant mixture was added dropwise a solution of 15 g of potassium hydroxide in 100 ml of water. The mixture was stirred at room temperature for 30 minutes and enough additional water was added to give a homogeneous solution. The mixture was stirred at room temperature for 16 hours and then poured into 4 liters of water. The yellow precipitate which formed was separated by filtration and dried to give 3-amino-6,7-dimethoxy thieno[2,3-b]quinoline-2-carboxamide melting at about 278.5°–279.5° C. with decomposition.

If the above procedure is repeated using 2-chloro-6,7-methylenedioxy-3-quinolinecarbonitrile and 2-chloro-6-methoxy-3-quinolinecarbonitrile, the products obtained are, respectively, 3-amino-6,7-methylenedioxythieno-

[2,3-b]quinoline-2-carboxamide and 3-amino-6-methoxythieno[2,3-b]quinoline-2-carboxamide.

EXAMPLE 4

To a solution of 5.0 g of 3-amino-6,7-dimethoxythieno[2,3-b]quinoline-2-carboxamide in 1.5 liters of glacial acetic acid was added dropwise a solution of 4.0 g of sodium nitrite in 20 ml of water. The resulting mixture was stirred at room temperature for 16 hours. The solvent was then evaporated from the reaction mixture under reduced pressure to concentrate it to a volume of 300 ml. The solid which formed was separated by filtration to give 8,9-dimethoxy-1,2,3-triazino[4',5':4,5]thieno[2,3-b]quinolin-4(3H)-one. A small portion of this product was washed with hot tetrahydrofuran to give an off-white solid melting at greater than 230° C. with decomposition. The product obtained has the following structural formula

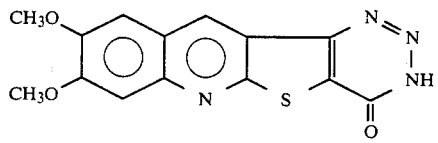

EXAMPLE 5

If the procedure of Example 4 is repeated using 3-amino-6,7-methylenedioxythieno[2,3-b]quinoline-2-carboxamide and 3-amino-6-methoxythieno[2,3-b]quinoline-2-carboxamide, the products obtained are, respectively, 8,9-methylenedioxy-1,2,3-triazino[4',5':4,5]thieno[2,3-b]quinolin-4(3H)-one and 9-methoxy-1,2,3-triazino[4',5':4,5]thieno[2,3-b]quinolin-4(3H)-one.

EXAMPLE 6

To a mixture of 8.8 g of 8,9-dimethoxy-1,2,3-triazino[4',5':4,5]thieno[2,3-b]quinolin-4(3H)-one and 12 g of potassium carbonate in 50 ml of dimethylformamide at 75° C. is added 6 ml of methyl iodide. Stirring at this temperature is continued for 3 hours. The mixture is then diluted with water and the precipitate which forms is separated by filtration to give 8,9-dimethoxy-3-methyl-1,2,3-triazino[4',5':4,5]thieno[2,3-b]quinolin-4(3H)-one.

What is claimed is:

1. A compound of the formula

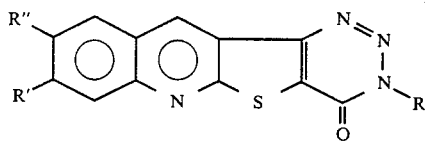

wherein R is hydrogen or alkyl of 1–4 carbon atoms; R' and R" are selected from hydrogen and methoxy with the proviso that only one of them can be hydrogen, or R' and R" are combined to give methylenedioxy.

2. A compound according to claim 1 which is 8,9-dimethoxy-1,2,3-triazino[4',5':4,5]thieno[2,3-b]-quinolin-4(3H)-one.

* * * * *